(12) United States Patent
Struble et al.

(10) Patent No.: US 11,289,176 B2
(45) Date of Patent: *Mar. 29, 2022

(54) DETERMINATION OF COPY NUMBER VARIATIONS USING BINOMIAL PROBABILITY CALCULATIONS

(71) Applicant: Ariosa Diagnostics, Inc., San Jose, CA (US)

(72) Inventors: Craig Struble, San Jose, CA (US); John Stuelpnagel, San Jose, CA (US)

(73) Assignee: Ariosa Diagnostics, Inc., San Jose, CA (US)

(*) Notice: Subject to any disclaimer, the term of this patent is extended or adjusted under 35 U.S.C. 154(b) by 763 days.

This patent is subject to a terminal disclaimer.

(21) Appl. No.: 14/176,830

(22) Filed: Feb. 10, 2014

(65) Prior Publication Data

US 2014/0180602 A1    Jun. 26, 2014

Related U.S. Application Data

(63) Continuation of application No. 13/605,505, filed on Sep. 6, 2012, now Pat. No. 8,712,697.

(60) Provisional application No. 61/531,738, filed on Sep. 7, 2011.

(51) Int. Cl.
| | | |
|---|---|---|
| G16B 5/20 | (2019.01) | |
| G16B 30/00 | (2019.01) | |
| G16B 20/10 | (2019.01) | |
| G16B 20/00 | (2019.01) | |
| G16B 20/20 | (2019.01) | |
| G16B 20/40 | (2019.01) | |

(52) U.S. Cl.
CPC .............. *G16B 5/20* (2019.02); *G16B 20/00* (2019.02); *G16B 20/10* (2019.02); *G16B 20/20* (2019.02); *G16B 30/00* (2019.02)

(58) Field of Classification Search
None
See application file for complete search history.

(56) References Cited

U.S. PATENT DOCUMENTS

| | | | |
|---|---|---|---|
| 5,876,924 A | 3/1999 | Zhang et al. | |
| 6,258,540 B1 | 7/2001 | Lo et al. | |
| 6,316,229 B1 | 11/2001 | Lizard et al. | |
| 6,911,345 B2 | 6/2005 | Quake et al. | |
| 6,927,028 B2 | 8/2005 | Lo et al. | |
| 7,645,576 B2 | 1/2010 | Lo et al. | |
| 7,709,194 B2 | 5/2010 | Lo et al. | |
| 7,718,367 B2 | 5/2010 | Lo et al. | |
| 7,754,428 B2 | 7/2010 | Lo et al. | |
| 7,888,017 B2 | 2/2011 | Quake et al. | |
| 7,901,884 B2 | 3/2011 | Lo et al. | |
| 8,008,018 B2 | 8/2011 | Quake et al. | |
| 8,195,415 B2 | 6/2012 | Fan et al. | |
| 8,293,076 B2 | 10/2012 | Fan et al. | |
| 8,318,430 B2 | 11/2012 | Chuu et al. | |
| 8,712,697 B2 | 4/2014 | Struble et al. | |
| 2002/0045176 A1 | 4/2002 | Lo et al. | |
| 2002/0132241 A1 | 9/2002 | Fan et al. | |
| 2002/0152035 A1 | 10/2002 | Perlin | |
| 2003/0003459 A1 | 1/2003 | Stahl | |
| 2003/0044388 A1 | 3/2003 | Lo et al. | |
| 2004/0009518 A1 | 1/2004 | Lo et al. | |
| 2004/0101835 A1 | 5/2004 | Willis et al. | |
| 2004/0203037 A1 | 10/2004 | Lo et al. | |
| 2006/0252068 A1 | 11/2006 | Lo et al. | |
| 2006/0252071 A1 | 11/2006 | Lo et al. | |
| 2007/0172873 A1 | 7/2007 | Brenner et al. | |
| 2007/0178478 A1 | 8/2007 | Dhallan | |
| 2007/0275402 A1 | 11/2007 | Lo et al. | |
| 2008/0081338 A1 | 4/2008 | Lo et al. | |
| 2008/0138809 A1 | 6/2008 | Kapur et al. | |
| 2008/0243398 A1 | 10/2008 | Rabinowitz | |
| 2009/0029377 A1 | 1/2009 | Lo et al. | |
| 2009/0048124 A1 | 2/2009 | Leamon et al. | |
| 2009/0061425 A1 | 3/2009 | Lo et al. | |
| 2009/0087847 A1 | 4/2009 | Lo et al. | |
| 2009/0099041 A1 | 4/2009 | Church et al. | |
| 2009/0155776 A1 | 6/2009 | Lo et al. | |
| 2010/0112575 A1 | 5/2010 | Fan et al. | |
| 2010/0112590 A1 | 5/2010 | Lo et al. | |
| 2010/0136529 A1 | 6/2010 | Shoemaker et al. | |
| 2010/0267034 A1 | 10/2010 | Lo et al. | |
| 2010/0273675 A1 | 10/2010 | Balis et al. | |
| 2010/0291571 A1 | 11/2010 | Stoughton et al. | |
| 2010/0291572 A1 | 11/2010 | Stoughton et al. | |
| 2011/0003293 A1 | 1/2011 | Stoughton et al. | |
| 2011/0027771 A1 | 2/2011 | Deng | |
| 2011/0086357 A1 | 4/2011 | Lo et al. | |
| 2011/0105353 A1 | 5/2011 | Lo et al. | |

(Continued)

FOREIGN PATENT DOCUMENTS

| | | |
|---|---|---|
| WO | WO2008/118998 | 10/2008 |
| WO | WO2009/036525 | 3/2009 |

OTHER PUBLICATIONS

Bianchi, et al., "Large Amounts of Cell-free DNAS Are Present in Amniotic Fluid", Clin. Chem., 47(10) 1867-69 (2001).

(Continued)

*Primary Examiner* — Olivia M. Wise
(74) *Attorney, Agent, or Firm* — Mintz Levin Cohn Ferris Glovsky and Popeo, P.C.

(57) ABSTRACT

This invention relates to a binomial calculation of copy number of data obtained from a mixed sample having a first source and a second source.

14 Claims, 1 Drawing Sheet

(56) References Cited

U.S. PATENT DOCUMENTS

| | | |
|---|---|---|
| 2011/0143342 A1 | 6/2011 | Lo et al. |
| 2011/0151442 A1 | 6/2011 | Fan et al. |
| 2011/0171638 A1 | 7/2011 | Stoughton et al. |
| 2011/0177517 A1 | 7/2011 | Rava et al. |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0245085 A1 | 10/2011 | Rava et al. |
| 2011/0276277 A1 | 11/2011 | Lo et al. |
| 2011/0312503 A1 | 12/2011 | Chuu |
| 2012/0003650 A1 | 1/2012 | Lo et al. |
| 2012/0010085 A1 | 1/2012 | Rava |
| 2012/0034603 A1 | 2/2012 | Oliphant et al. |
| 2012/0039724 A1 | 2/2012 | Rossi |
| 2012/0100548 A1 | 4/2012 | Rava et al. |
| 2012/0108460 A1 | 5/2012 | Quake et al. |
| 2012/0165203 A1 | 6/2012 | Quake et al. |
| 2012/0184449 A1 | 6/2012 | Hixson |
| 2012/0190018 A1* | 7/2012 | Struble .................. G06F 19/18 435/6.11 |
| 2012/0191359 A1 | 7/2012 | Oliphant et al. |
| 2012/0191367 A1 | 7/2012 | Stuelpnagel et al. |
| 2012/0219950 A1 | 8/2012 | Oliphant et al. |
| 2012/0230258 A1 | 9/2012 | Miki |
| 2012/0237928 A1 | 9/2012 | Rava et al. |
| 2012/0264115 A1 | 10/2012 | Rava |
| 2012/0264121 A1 | 10/2012 | Rava et al. |
| 2012/0270739 A1 | 10/2012 | Rava et al. |
| 2013/0029852 A1 | 1/2013 | Rava |
| 2014/0188401 A1 | 7/2014 | Struble et al. |

OTHER PUBLICATIONS

Centre for Genomics Education, "Changes to Chromosome Structure—Translocations", The Australasian Genetics Resource Book, www.genetics.com, pp. 1-5 (2007).

Chiu, et al., "Non-invasive prenatal diagnosis by single molecule counting technologies", Trends in Genomics, 25(7):324-31 (2009).

Hayden, et al., "Multiplex-Ready PCR: A new method for multiplexed SSR and SNP genotyping", BMC Genomics, 9:80:1-12 (2007).

Hsuih, et al., "Novel, ligation-depdent PCR assay for detection of hepatitis C in serum", J. of Clin. Microbiology, 34(3):501-07 (1996).

Huang, et al., "Identification of a family of alternatively splied mRNA species of angiopoietin-1", Blood, 95:1993-99 (2000).

Indolfi, et al., "Perinatal Transmission of Hepatitis C Virus Infection", J. Med. Virol., 81:836-43 (2009).

Mardis, et al., "The impact of next-generation sequencing technology on genetics", Trends in Genetics, 24(3):133-41 (2007).

Porreca, et al., "Multiplex amplification of large sets of human exons", Nat. Methods, 4(11):931-36 (2007).

Schouten, et al., "Relative quantification of 40 nucleic acid sequences by multiplex ligation-dependent probe amplification", Nuc. Ac. Res., 30(12):e57 (2002).

Tewhey, et al., "Microdroplet-based PCR enrichment for large-scale targeted sequencing", Nat. Biotech., 27(11):1025-31 (2009).

Zolotukhina, et al., "Analysis of Cell-free DNA in Plasma and Serum of Pregnant Women", J. of Hist. and Cytochem., 53:297-99 (2005).

Office Action dated Oct. 31, 2013 for U.S. Appl. No. 13/356,575, filed Jan. 23, 2012, inventor Oliphant, entire document.

Office Action dated Jun. 25, 2014 for U.S. Appl. No. 13/689,206, filed Nov. 29, 2012, inventor Oliphant, entire document.

Office Action dated Feb. 11, 2014 for U.S. Appl. No. 13/689,206, filed Nov. 29, 2012, inventor Oliphant, entire document.

Office Action dated Jun. 26, 2014 for U.S. Appl. No. 13/356,133, filed Jan. 23, 2012, inventor Oliphant, entire document.

Office Action dated Oct. 18, 2013 for U.S. Appl. No. 13/356,133, filed Jan. 23, 2012, inventor Oliphant, entire document.

Office Action dated Jul. 31, 2013 for U.S. Appl. No. 13/013,732, filed Jun. 25, 2011, inventor Oliphant, entire document.

Office Action dated Apr. 14, 2014 for U.S. Appl. No. 13/013,732, filed Jun. 25, 2011, inventor Oliphant, entire document.

Office Action dated Feb. 11, 2014 for U.S. Appl. No. 13/405,839, filed Feb. 27, 2012, inventor Oliphant, entire document.

Office Action dated Oct. 25, 2013 for U.S. Appl. No. 13/407,978, filed Feb. 29, 2012, inventor Song, entire document.

Office Action dated Jul. 30, 2014 for U.S. Appl. No. 13/407,978, filed Feb. 29, 2012, inventor Song, entire document.

Office Action dated Jan. 31, 2014 for U.S. Appl. No. 13/605,505, filed Sep. 6, 2012, inventor Struble, entire document.

Office Action dated Aug. 8, 2013 for U.S. Appl. No. 13/605,505, filed Sep. 6, 2012, inventor Struble, entire document.

Office Action dated Aug. 30, 2013 for U.S. Appl. No. 13/687,169, filed Nov. 28, 2012, inventor Sparks, entire document.

Office Action dated May 8, 2014 for U.S. Appl. No. 13/687,169, filed Nov. 28, 2012, inventor Sparks, entire document.

Office Action dated Dec. 10, 2013 for U.S. Appl. No. 13/205,490, filed Aug. 8, 2011, inventor Sparks, entire document.

Office Action dated Jul. 8, 2013 for U.S. Appl. No. 13/205,490, filed Aug. 8, 2011, inventor Sparks, entire document.

Office Action dated Oct. 2, 2013 for U.S. Appl. No. 13/687,025, filed Nov. 28, 2012, inventor Sparks, entire document.

Office Action dated Jul. 16, 2014 for U.S. Appl. No. 13/687,025, filed Nov. 28, 2011, inventor Sparks, entire document.

Office Action dated Aug. 30, 2013 for U.S. Appl. No. 13/205,570, filed Aug. 8, 2011, inventor Sparks, entire document.

Office Action dated May 8, 2014 for U.S. Appl. No. 13/205,570, filed Aug. 8, 2011, inventor Sparks, entire document.

Office Action dated Jul. 14, 2014 for U.S. Appl. No. 13/293,419, filed Nov. 10, 2011, Sparks, entire document.

Office Action dated Jun. 26, 2014 for U.S. Appl. No. 13/205,603, filed Aug. 8, 2011, inventor Sparks, entire document.

Office Action dated Dec. 30, 2013 for U.S. Appl. No. 13/205,603, filed Aug. 8, 2011, inventor Sparks, entire document.

Office Action dated Dec. 11, 2013 for U.S. Appl. No. 13/274,309, filed Oct. 15, 2011, inventor Struble, entire document.

Office Action dated Aug. 30, 2013 for U.S. Appl. No. 13/245,133, filed Sep. 26, 2011, inventor Oliphant, entire document.

Office Action dated Feb. 28, 2013 for U.S. Appl. No. 13/245,133, filed Sep. 26, 2011, inventor Oliphant, entire document.

Office Action dated May 8, 2014 for U.S. Appl. No. 13/245,133, filed Sep. 26, 2011, inventor Oliphant, entire document.

Office Action dated May 12, 2014 for U.S. Appl. No. 13/689,417, filed Nov. 29, 2012, inventor Oliphant, entire document.

Office Action dated Oct. 31, 2013, filed Dec. 9, 2011, inventor Oliphant for U.S. Appl. No. 13/316,154, entire document.

Australian Patent Examination Report No. 1 dated Feb. 20, 2014 for 2011285512, entire document.

Australian Patent Examination Report No. 1 dated Mar. 4, 2014 for 2011285518, entire document.

Australian Patent Examination Report No. 1 dated Feb. 7, 2014 for 2011285477, entire document.

EPO Examination Report dated Nov. 21, 2013 for App. No. 11745880.2, entire document.

EPO Examination Report dated Nov. 21, 2013 for App. No. 11745881.1, entire document.

EPO Examination Report dated Nov. 28, 2013 for App. No. 11745883.6, entire document.

Search Report dated Sep. 12, 2013 for PCT/US 2012/026754, entire document.

Search Report dated Nov. 15, 2013 for PCT/US 2013/51310, entire document.

Search Report dated May 14, 2013 for PCT/US 2014/17092, entire document.

Chiu, et al, "Effects of Blood-Processing Protocols on Fetal and Total DNA Quantification in Maternal Plasma", Clin. Chem., 47(9):1607-1613 (2001).

Chiu, et al., "Maternal plasma DNA analysis with massively parallel sequencing by ligation for noninvasive prenatal diagnosis of trisomy 21", 56:459-63 (2010).

(56) References Cited

OTHER PUBLICATIONS

Chiu, et al, "Noninvasive prenatal diagnosis of fetal chromosomal aneuploidy by massively parallel genomic sequencing of DNA in maternal plasma", PNAS USA 105:20458-63 (2008).
Chiu and Lo, "Non-invasive prenatal diagnosis by fetal nucleic acid analysis in maternal plasma: the coming of age", Semin. Fetal Neonatal Med., 16(2):88-93 (2011).
Chiu, et al., "Non-invasive prenatal assessment of trisomy 21 by multiplexed maternal plasma DNA sequencing: large scale validity study", Br Med J. 342:c7401 (2011).
Chiu, et al., "Noninvasive prenatal diagnosis of fetal chromosomal aneuploidy by massively parallel genomic sequencing of DNA in maternal plasma", PNAS USA 105:20458-63 (2008) Supporting Information.
Fan, et al., "Noninvasive diagnosis of fetal aneuploidy by shotgun sequencing DNA from maternal blood", PNAS USA, 105(42):16266-71 (2008).
Fan, et al., "Analysis of the Size Distributions of Fetal and Maternal Cell-Free DNA by Paired-End Sequencing", Clin. Chem., 56(8):1279-80 (2010).
Fan, et al., "Sensitivity of noninvasive prenatal detection of fetal aneuploidy from maternal plasma using shotgun sequencing is limited only by counting statistics", PLoS One, 5:e10439 (2010).
Lo, et al., "Detection of single-copy fetal DNA sequence from maternal blood", The Lancet, 335:1463-64 (1990).
Lo, et al., "Two-way cell traffic between mother and fetus: biological and clinical implications", Blood, 88:4390-95 (1996).
Lo, et al., "Presence of fetal DNA in maternal plasma and serum", The Lancet, 350:485-86 (1997).
Lo, et al., "Quantitative analysis of fetal DNA in maternal plasma and serum: implications for noninvasive prenatal diagnosis", Am J. Hum. Genetics, 62:768-75 (1998).
Lo, et al., "Prenatal diagnosis of fetal RhD status by molecular analysis of maternal plasma", N Engl J Med, 339:1734-38 (1998).
Lo, et al., "Rapid clearance of fetal DNA from maternal plasma", Am J. Hum. Genetics, 64:218-24 (1999).
Lo, et al., "Digital PCR for the molecular detection of fetal chromosomal aneuploidy", PNAS USA, 104:13116-21 (2007).
Lo, et al., "Plasma placental RNA allelic ratio permits noninvasive prenatal chromosomal aneuploidy detection", Nat. Med., 13:218-23 (2007).
Lo, et al., Maternal plasma DNA sequencing reveals the genome-wide genetic and mutational profile of the fetus. Sci Transl Med, 2:61ra91 (2010).
Lo, "Fetal nucleic acids in maternal blood: the promises", Clin. Chem. Lab Med., 50(5):xxx-xxx (DOI 10.1515/CCLM.2011.765) (2011).
Poon, et al., "Differential DNA methylation between fetus and mother as a strategy for detecting fetal DNA in maternal plasma", Clin Chem, 48:35-41 (2002).
Ashoor, et al., Fetal Fraction in Maternal Plasma Cell-Free DNA at 11-13 Weeks' Gestation: Effect of Maternal and Fetal Factors, Fetal Dian Ther DOI:10.1159/000337373, entire document (Pub'd online May 4, 2012).
Ashoor, et al., "Chromosome-selective sequencing of maternal plasma cell-free DNA for first-trimester detection of trisomy 21 and trisomy 18", Am. J. of Obstet. Gynecol., doi: 10.1016/j.ajog.2012.01.029, entire document (2012).
Cirigiliano, et al., "Rapid prenatal diagnosis of common chromosome aneuploidies by QF-PCR, results of 9 years of clinical experience", Prenatal diagnosis, 29:40-49 (2009).
Dhallan, et al., "A non-invasive test for prenatal diagnosis based on fetal DNA present in maternal blood: a preliminary study", Lancet, 369(9560):474-81 (2007).
Ehrich, et al., "Noninvasive detection of fetal trisomy 21 by sequencing of fetal DNA in maternal blood: a study in a clinical setting", AM J. Obstet Gynecol, 2011:204:205 e1-11 (2011).
Enders, et al., "Fetal morbidity and mortality after acute human parvovirus B19 infection in pregnancy: prospective evaluation of 1018 cases", Prenatal Diagnosis, 24:513-18 (2004).

Smith, et al., "Quantitative phenotyping via deep barcode sequencing", Genome Res., 19:1836-42 (2009).
Van Opstal, et al., "Rapdi aneuploidy detection with multiplex ligation-dependent probe amplification: a prospective study of 4000 amniotice fluid samples", Eur. J. of Hum. Genetics, 17:112-21 (2009).
Xie and Tammi, "CNV-seq, a new method to detect copy number variation using high throughput sequencing", BMC Bioinformatics, 10:80 (2008), doi 10.1186/1471-2105-10-80, p. 1-9.
Young and Davis, "Efficient isolation of genes by using antibody probes", PNAS 80:1194-98 (1983).
Search Report dated Jan. 20, 2012 for (PCT/US2012/21955), entire document.
Search Report dated May 2, 2012 for PCT/US2011/046935), entire document.
Search Report dated May 10, 2012 for (PCT/US2012/026754), entire document.
Search Report dated May 11, 2012 for (PCT/US2012/022261), entire document.
Search Report dated Aug. 13, 2012 for (PCT/US2011/046976), entire document.
Search Report dated Oct. 15, 2012 for (PCT/US2011/046981), entire document.
Search Report dated Feb. 21, 2013 for (PCT/US2011/046963), entire document.
Search Report dated Apr. 19, 2013 for (PCT/US2012/70177), entire document.
Search Report dated Aug. 12, 2014 for PCT/US2013/75683, entire document.
Office Action dated Apr. 15, 2013 for U.S. Appl. No. 13/356,133, inventor A. Oliphant, filed Jan. 23, 2012), entire document.
Office Action dated May 17, 2013 for U.S. Appl. No. 13/356,575, inventor A. Oliphant, filed Jan. 23, 2012), entire document.
Office Action dated Apr. 5, 2013 for U.S. Appl. No. 13/689,206, inventor A. Oliphant, filed 39 Nov. 2012), entire document.
Final Office Action dated Jul. 8, 2013 for U.S. Appl. No. 13/689,206, inventor A. Oliphant, filed 39 Nov. 2012), entire document.
Office Action dated Jul. 5, 2012 for U.S. Appl. No. 13/013,732, inventor A. Oliphant, filed Jun. 25, 2011), entire document.
Office Action dated Dec. 7, 2012 for U.S. Appl. No. 13/013,732, inventor A. Oliphant, filed Jun. 25, 2011), entire document.
Office Action dated Apr. 11, 2013 for U.S. Appl. No. 13/013,732, inventor A. Oliphant, filed Jun. 25, 2011), entire document.
Office Action dated May 13, 2013 for U.S. Appl. No. 13/407,978, inventor K. Song, filed Feb. 29, 2012), entire document.
Office Action dated Jul. 8, 2013 for U.S. Appl. No. 13/205,490, inventor A. Sparks, filed Aug. 8, 2011), entire document.
Office Action dated Mar. 28, 2013 for U.S. Appl. No. 13/687,169, inventor A. Sparks, filed Nov. 28, 2012), entire document.
Office Action dated Feb. 28, 2013 for U.S. Appl. No. 13/205,570, inventor A. Sparks, filed Aug. 8, 2011), entire document.
Office Action dated Mar. 14, 2013 for U.S. Appl. No. 13/687,025, inventor A. Sparks, filed Nov. 28, 2012), entire document.
Office Action dated May 10, 2012 for U.S. Appl. No. 13/293,419, inventor A. Sparks, filed Nov. 10, 2011), entire document.
Office Action dated Aug. 22, 2012 for U.S. Appl. No. 13/293,419, inventor A. Sparks, filed Nov. 10, 2011), entire document.
Final Office Action dated Oct. 12, 2012 for U.S. Appl. No. 13/293,419, inventor A. Sparks, filed Nov. 10, 2011), entire document.
Advisory Action dated Jan. 29, 2013 for U.S. Appl. No. 13/293,419, inventor A. Sparks, filed Nov. 10, 2011), entire document.
Office Action dated Feb. 28, 2013 for U.S. Appl. No. 13/245,133, inventor A. Oliphant, filed Sep. 26, 2011), entire document.
Office Action dated Jun. 13, 2013 for U.S. Appl. No. 13/316,154, inventor A. Oliphant, filed Dec. 9, 2011), entire document.
Office Action dated Jun. 13, 2013 for U.S. Appl. No. 13/338,963, inventor A. Oliphant, filed Dec. 28, 2011), entire document.
Office Action dated Feb. 15, 201 for U.S. Appl. No. 13/689,417, inventor A. Oliphant, filed Nov. 29, 2012) entire document.
Tewhey, R. et al. (2009, e-published Nov. 1, 2009). "Microdroplet-based PCR enrichment for large-scale targeted sequencing," Nat Biotechnol 27(11):1025-1031; Supplementary materials: 33 pages.

(56) References Cited

OTHER PUBLICATIONS

Freedman, D. et al. (1991). Statistics: Second Edition. New York: W.W. Norton & Company, p. 241.
Wong, K.K. et al. (Jan. 2007, e-published Dec. 5, 2006). "A comprehensive analysis of common copy-number variations in the human genome," *Am J Hum Genet* 80(1):91-104.

* cited by examiner

DETERMINATION OF COPY NUMBER VARIATIONS USING BINOMIAL PROBABILITY CALCULATIONS

CROSS-REFERENCE TO RELATED APPLICATIONS

The present application is a continuation application of U.S. Ser. No. 13/605,505, filed Sep. 6, 2012, which claims priority to U.S. Ser. No. 61/531,738, filed Sep. 7, 2011, both of which are incorporated by reference.

FIELD OF THE INVENTION

This invention relates to processes using binomials for providing best fit probabilities for data sets.

BACKGROUND OF THE INVENTION

In the following discussion certain articles and processes will be described for background and introductory purposes. Nothing contained herein is to be construed as an "admission" of prior art. Applicant expressly reserves the right to demonstrate, where appropriate, that the articles and processes referenced herein do not constitute prior art under the applicable statutory provisions.

Recent advances in diagnostics have focused on less invasive mechanisms for determining disease risk, presence and prognosis. Diagnostic processes for determining genetic anomalies have become standard techniques for identifying specific diseases and disorders, as well as providing valuable information on disease source and treatment options.

Characterization of cell free nucleic acids in biological samples such as blood and plasma allows for less invasive techniques such as blood extraction to be used in making clinical decisions. For example, cell free DNA from malignant solid tumors has been found in the peripheral blood of cancer patients; individuals who have undergone organ transplantation have cell free DNA from the transplanted organ present in their bloodstream; and cell-free fetal DNA and RNA have been found in the blood and plasma of pregnant women. In addition, detection of nucleic acids from infectious organisms, such as viral or bacterial pathogens, provides important diagnostic and prognostic indicators.

However, the sensitivity of such testing is often dependent upon the identification of the amount of nucleic acid from the different sources, and in particular identification of a low level of nucleic acid from one source against a background of a much higher level of nucleic acids from a second source (e.g., fetal DNA in maternal plasma or viral nucleic acids in a patient sample). Determining the contribution of the minor nucleic acid species to the total nucleic acids present in the biological sample permits more accurate statistical interpretation of the resulting data.

In the case of copy number variants or aneuploidies, the portion of the chromosome with the copy number variant or the aneuploid chromosome may be genotypically identical to the background maternal DNA, hence fetal inheritance of an extra chromosome or portion thereof cannot be established merely by detecting the presence of nucleic acid sequences from the extra chromosome in the maternal sample.

There is thus a need for processes for calculating copy number variation (CNV) in one or more genomic regions in a biological sample using information on contribution of nucleic acids in the sample.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention relates to processes for identifying copy number variation (CNV) in one or more genomic regions. The methods of the invention comprise 1) calculating the estimated contribution of a first source and a second source in a mixed sample; and 2) calculating CNV for one or more genomic regions in the second source based on frequency data for the genomic regions and estimated source contribution.

The processes of the invention utilize binomial probability distributions of distinguishing regions in informative loci to determine the relative contribution of the loci from different sources in a mixed sample. CNV for a genomic region can be determined based on a comparison of the source contribution in a mixed sample to empirical copy numbers for a selected locus from a source in the mixed sample. The source contribution used for comparison is preferably the source for which the CNV is being determined.

CNV can also be based on the frequency data of the selected loci from a reference mixed sample having a source contribution substantially the same as the source contribution of the mixed sample from which the empirical copy numbers for a selected locus are obtained.

The processes and systems of the invention allow identification of CNV for larger genomic regions (e.g., genomic regions encompassing multiple loci). This can be accomplished using two or more loci that are present in the genomic region or associated with the genomic region. Information on the frequency of a set of loci can determine not only the CNV for a particular genomic region, but in certain embodiments it can also determine the relative boundaries of the region by selection of particular loci in a set present in or around such boundaries.

In a first implementation, the invention provides a process for estimating the CNV of a selected locus by 1) calculating the source contribution of a first source and/or a second source in a mixed sample using frequency data derived from two or more informative loci; and 2) identifying a CNV for one or more genomic regions in the second source by comparing copy number of the genomic region from the second source in the mixed sample to the source contribution in the mixed sample. The source contribution used for comparison is preferably the contribution of the second source. In a preferred embodiment, the source contribution is determined through identification of distinguishing regions on copies of the informative loci in the cell free nucleic acids in the mixed sample.

In a specific aspect, the source contribution in the mixed sample is calculated by sequencing one or more distinguishing regions of informative loci copies present in a mixed sample and measuring the frequency of the copies present in the mixed sample. The frequency of loci can be measured as "counts", i.e., the number of the particular alleles of the informative loci identified in the mixed sample. The binomial distribution calculation is carried out using the counts of the alleles of the informative loci from the first source and the second source in a mixed sample. An estimate of the contribution of the first source nucleic acids and/or the second source nucleic acids can thus be calculated from these frequency data sets. The counts can be based on raw data, or the counts may be normalized to take into account experimental variation.

The required number of informative loci for an accurate determination of copy number variation in a genomic region depends upon a number of variables, as will be apparent to one skilled in the art upon reading the present disclosure. In general, enough loci need to be used to have statistical power to detect copy number variants of one or more genomic regions as compared to the source contribution of the second source. The variables that affect statistical power include source contribution of the different sources in the mixed sample and variation of copy numbers between informative loci used to determine source contribution in a mixed sample. In a preferred aspect, the selected locus for which CNV is being interrogated is not used as an informative locus for the calculation of source contribution in the mixed sample, although in certain aspects the selected locus can be included in the frequency data used for this calculation.

In certain aspects, copy number variation for a genomic region can be determined by directly comparing the frequency of the locus or loci in a mixed sample to the source contribution in the mixed sample, and preferably to the contribution of the second source in the mixed sample. The frequency of the one or more loci can be determined through various means known to those skilled in the art. In certain embodiments, a single empirical assay is used to determine both source contribution and the copy number of one or more loci in the mixed sample. Copy number variation can then be determined based on mathematical modeling of the different frequency data obtained from the results of the single assay, as described in more detail herein. In other aspects, the copy number of the one or more genomic regions can be determined using a separate assay on the mixed sample, and the information input for calculation of the CNV of the loci in the mixed sample.

In a preferred embodiment, the copy number variation is determined for a larger genomic region in a mixed sample using a comparative of two or more, and preferably five or more, selected loci in a mixed sample. The CNV for the genomic region is preferably determined using a statistical method such as Markov modeling. A Markov model is a stochastic model that assumes the Markov property, i.e., the conditional probability distribution of future states of the process, given the present state and the past states, depend only upon the present state. In the Markov process, the past is irrelevant because it does not affect how the current state was obtained. Generally, this assumption enables reasoning and computation with the model that would otherwise be intractable. For exemplary modeling, see e.g., Wang K., Genome Res. 2007 17: 1665-1674. In such embodiments, the copy number of loci within or associated with a genomic section in a mixed sample are measured empirically, and compared to the source contribution in the mixed sample. Thus, the invention provides a process for utilizing data sets of counts for one or more distinguishing regions of two or more informative loci to derive source contribution from two or more sources of cell free nucleic acids within a mixed sample.

In one specific aspect, the mixed sample is a maternal sample comprising maternal and fetal cell free nucleic acids. The source contribution is derived using counts of maternal and fetal cell free nucleic acids from cell free DNA ("cfDNA") in the mixed sample.

In one implementation, the invention provides a computer-implemented process for estimating the CNV for one or more genomic regions from a single source in a mixed sample, wherein at least one processor coupled to a memory executes a software component that performs the process comprising: accessing by the software component a first data set comprising frequency data for two or more informative loci from a first source; accessing by the software component a second data set comprising frequency data for two or more informative loci from a second source; calculating source contribution based on a binomial distribution of distinguishing regions from first and second data sets; and calculating the CNV for a genomic region by comparison of the frequency data of the genomic region in the mixed sample to the source contribution. Preferably, the CNV of a genomic region from the second source is calculated by comparing the relative frequency of the selected locus to source contribution of the second source in the mixed sample.

In certain embodiments using a set of loci to determine the CNV of a larger genomic region in a single source, the CNV is calculated using a binomial probability calculation of loci copy numbers in the mixed samples. The frequency of a first locus that is putatively normal in the mixed sample can be compared to the frequency of a second locus interrogated for CNV in the mixed sample, and the likelihood that the second locus displays a copy number variation can be based on the loci comparison as informed by the contribution of the source to the mixed sample.

In the various embodiments, the copy number of a genomic region for which CNV is calculated is introduced to the processor as a separate data set from the information used to calculate source contribution. In other embodiments, the copy number of a genomic region is a subset of the frequency data of the first and/or second data set used for calculation of source contribution, and the information is drawn from this data set for the calculation of CNV for the selected locus.

In a preferred implementation of the process and the systems of the invention, the calculations for determination of source contribution and/or for determination of CNV are performed using an algorithm that calculates a binomial probability distribution based on the frequency data from the first and/or second data sets. The contribution of the loci from the first and second sources in a mixed sample can be estimated by calculating the maximum likelihood estimate based on the frequency of the informative loci from the first source and the second source. In a more specific implementation, the maximum likelihood estimate is modeled by the equation:

$$\text{Binomial}(A, B, p) = \frac{(A+B)!}{A!B!} p^A (1-p)^B$$

wherein A is the quantity of copies of an informative locus from the second source, B is the quantity of copies of an informative locus from the first source, and p is the maximum likelihood estimate for the binomial distribution with quantities A and B.

The probability p corresponding to the maximum likelihood estimate is calculated within a machine environment using an optimization algorithm. Examples of optimization algorithms include, but are not limited to, gradient descent, simulated annealing, and evolutionary algorithms.

Preferably, the frequency data sets from the first and second sources are used to calculate source contribution using a first binomial distribution, and a subset of the frequency data is used to calculate CNV for one or more selected loci using a second binomial distribution calculation. The frequency data used for the CNV may or may not distinguish counts for a locus based on locus source. Thus, in some aspects the CNV is detected using total counts of one or more loci from a mixed sample without regard as to the source of the locus in the mixed sample.

In one aspect, the invention provides processes for estimating CNV of one or more genomic regions using cell free nucleic acids in a mixed sample from an individual, the sample comprising cell free nucleic acids from both normal and putative genetically atypical cells. Such samples include, but are not limited to, samples comprising maternal and fetal cell free nucleic acids and samples that contain cell free nucleic acids from normal cells and cancerous cells.

In another aspect, the invention provides processes for estimating CNV of genomic regions in mixed samples comprising cell free nucleic acids from two or more different organisms in a sample from a single individual, e.g., mammalian nucleic acids from the host and nucleic acids from an infectious organism (e.g., bacterial, fungal or viral nucleic acids).

In yet another aspect, the invention provides processes for estimating CNV of genomic regions in mixed samples comprising cell free nucleic acids from a donor cell source and a host recipient cell source, e.g., cells from a transplant recipient and donor cells from the transplanted organ.

In another implementation the invention provides a computer-implemented process for calculating the copy number variation of a genomic region in a mixed sample, the process comprising: accessing by the software component a first data set comprising frequency data based on identification of one or more distinguishing regions of two or more informative loci from a first source in the sample; accessing by the software component a second data set comprising frequency data based on identification of one or more distinguishing regions of two or more informative loci from a second source in the sample; calculating the source contribution of cell free nucleic acids from the mixed sample; and calculating variation of the copy number of a genomic region in the sample by comparison of the copy number of the genomic region in the first source with the source contribution of cell free nucleic acids. Preferably, the copy number of the genomic region in the second source is compared with the source contribution of the second source in the mixed sample. The contribution of the cell free nucleic acids from the first and/or second sources are preferably calculated based on a binomial distribution of the counts of the distinguishing regions from the first and second data sets.

In a more specific implementation, the invention provides a computer-implemented process for calculating the contribution of cell free nucleic acids from a maternal source and a fetal source in a maternal sample, the system comprising: accessing by the software component a first data set comprising frequency data based on identification of one or more distinguishing regions of two or more informative loci from the maternal source in the sample; accessing by the software component a second data set comprising frequency data based on identification of one or more distinguishing regions in two or more informative loci of the fetal source in the sample; calculating the contribution of cell free nucleic acids in the maternal sample; and calculating variation of the copy number of the genomic region in the maternal sample by comparison of the copy number of a selected locus with the source contribution of cell free nucleic acids The source contribution of the cell free nucleic acids is preferably based on a binomial distribution of the counts of the distinguishing regions from the first and second data sets. Preferably, the CNV of a fetal nucleic acid is determined based on comparison of the locus frequency with the fetal source contribution in the mixed sample.

The calculation of the contribution of cell free nucleic acids in the mixed sample is preferably based on counts of the informative loci determined using a single assay system. In certain embodiments, the frequency of selected loci for the mixed sample is determined empirically using a separate assay from that used to determine the source contribution of the different sources in the mixed sample. In some embodiments, the copy number variation of the genomic region may be determined using reference frequencies of the selected loci for mixed samples with certain calculations of source contribution from the different sources.

In another implementation, the invention provides an executable software product stored on a computer-readable medium containing program instructions for determining CNV in a mixed sample, the program comprising instructions for: accessing by the software component a first data set comprising frequency data based on identification of distinguishing regions from copies of two or more informative loci from a first source; accessing by the software component a second data set comprising frequency data based on identification of distinguishing regions from copies of two or more informative loci from a second source; calculating the source contribution of cell free nucleic acids from the first source and/or second source based on a binomial distribution of the first and second data sets; and calculating variation of the copy number of one or more genomic regions in the sample by comparison of the copy number of one or more genomic regions with the contribution of cell free nucleic acids from the first source and/or second source.

In still another implementation, the invention provides an executable software product stored on a computer-readable medium containing program instructions for determining CNV for a genomic region in a maternal sample, the program comprising instructions for: accessing by the software component a first data set comprising frequency data based on identification of distinguishing regions from copies of two or more informative loci from a maternal source; accessing by the software component a second data set comprising frequency data based on identification of distinguishing regions from copies of two or more informative loci from a fetal source; calculating the source contribution of cell free nucleic acids from the maternal source and/or fetal source based on a binomial distribution of the first and second data sets; and calculating variation of the copy number of one or more genomic regions in the maternal sample by comparison of the copy number of the one or more genomic regions with the contribution of cell free nucleic acids from the maternal source and/or fetal source.

In another implementation, the invention provides an executable software product stored on a computer-readable medium containing program instructions for determining CNV for a genomic region in a mixed sample, the program comprising instructions for: accessing by the software component a first data set comprising frequency data based on identification of distinguishing regions from copies of two or more informative loci from a first source; accessing by the software component a second data set comprising frequency data based on identification of distinguishing regions from copies of two or more informative loci from a second source; calculating a source contribution of cell free nucleic acids from the first source and/or second source based on a binomial distribution of the first and second data sets; and calculating variation of the copy number of a genomic region by comparison of the copy number of a set of selected loci with the source contribution of cell free nucleic acids from the first source and/or second source.

In another implementation, the invention provides an executable software product stored on a computer-readable medium containing program instructions for determining CNV for a genomic region in a maternal sample, the program comprising instructions for: accessing by the software component a first data set comprising frequency data based on identification of distinguishing regions from copies of two or more informative loci from a maternal source; accessing by the software component a second data set comprising frequency data based on identification of distinguishing regions from copies of two or more informative loci from a fetal source; calculating the source contribution of cell free nucleic acids from the maternal source and/or fetal source based on a binomial distribution of the first and second data sets; and calculating variation of the copy number of a genomic region by comparison of the copy number of a set of selected loci with the source contribution of cell free nucleic acids from the maternal source and/or fetal source.

In yet another implementation, the invention provides a system comprising: a memory; a processor coupled to the memory; and a software component executed by the processor that is configured to access a first data set comprising frequency data for at least one distinguishing region from two or more informative loci from a first source in a mixed sample; input a second data set comprising frequency data for at least one distinguishing region from two or more informative loci from a second source in the mixed sample; calculate an estimated contribution of cell free nucleic acids from the first source and/or second source based on a binomial distribution of counts of the distinguishing regions from the first and second data sets; and calculate variation of the copy number of one or more genomic regions in the mixed sample by comparison of the copy number of the one or more selected loci with the estimated contribution of cell free nucleic acids in the mixed sample. In certain embodiments, the copy number of the selected loci corresponding to a genomic region is input as a separate data set. In other embodiments, the copy number of the selected loci corresponding to a genomic region is a subset of the first and/or second data set.

In a specific aspect the invention provides a computer software product including a non-transitory, computer-readable storage medium having fixed therein a sequence of instructions is executed by a computer direct performance of steps of: creating a first data set representing a quantity of copies of an informative locus from a first source in a mixed sample; creating a second data set representing a quantity of copies of informative locus from a second source in a mixed sample; calculating a source contribution of cell free nucleic acids based on a binomial distribution of distinguishing regions from first and second data sets; and determining the copy number variation of a genomic region in the mixed sample.

It is a feature of the invention that the calculation of source contribution of cell free nucleic acids can be optimized through summing the measured counts of informative loci, including the loci for which CNV is calculated.

It is another feature that the copy number of the genomic region may be empirically derived in the same assay used to determine source contribution in a mixed sample.

It is another feature that the copy number of the genomic region can be based on a reference number indicative of a likely frequency range of one or more selected loci corresponding to such genomic region for mixed samples such as those being analyzed.

These and other implementations, aspects, features and advantages will be provided in more detail as described herein.

DETAILED DESCRIPTION

The exemplary embodiments set forth herein relate to estimating the source contribution of cell free nucleic acids in a mixed sample, and using this information in the determination of a CNV of one or more loci in a single source of a mixed sample. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular processes and systems provided in particular implementations. However, the processes and systems will operate effectively in other implementations. Phrases such as "exemplary embodiment", "one embodiment" and "another embodiment" may refer to the same or different embodiments. The embodiments will be described with respect to systems and/or devices having certain components. However, the systems and/or devices may include more or less components than those shown, and variations in the arrangement and type of the components may be made without departing from the scope of the invention.

The exemplary embodiments will also be described in the context of particular processes having certain steps. However, the process and system operate effectively for other processes having different and/or additional steps and steps in different orders that are not inconsistent with the exemplary embodiments. Thus, the present invention is not intended to be limited to the embodiments shown, but is to be accorded the widest scope consistent with the principles and features described herein and as limited only by appended claims.

It should be noted that as used herein and in the appended claims, the singular forms "a," "and," and "the" include plural referents unless the context clearly dictates otherwise. Thus, for example, reference to "an informative locus" refers to one, more than one, or combinations of such loci, and reference to "a system" includes reference to equivalent steps and processes known to those skilled in the art, and so forth.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein are incorporated by reference for the purpose of describing and disclosing the formulations and processes that are described in the publication and which might be used in connection with the presently described invention.

Definitions

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "distinguishing region" refers to a region that is measurably different between loci. Such differences include, but are not limited to, single nucleotide polymorphisms (SNPs), differences in methylation status, mutations including point mutations and indels, short tandem repeats, copy number variants, and the like.

The term "genomic region" as used herein refers to any region of one or more loci that are normally found in a contiguous fashion in a genome. A genomic region may vary in size up to and including an entire chromosome.

The term "informative locus" as used herein refers to a locus with one or more distinguishing regions which is homozygous in one source and heterozygous in the other source within a mixed sample.

The terms "locus" and "loci" as used herein refer to a nucleic acid region of known location in a genome.

The term "maternal sample" as used herein refers to any sample taken from a pregnant mammal which comprises a maternal first source and a fetal second source of cell free nucleic acids (e.g., RNA or DNA).

The term "mixed sample" as used herein refers to any sample comprising cell free nucleic acids (e.g., DNA) from two or more sources in a single individual which can be distinguished based on informative loci. Exemplary mixed samples include a maternal sample (e.g., maternal blood, serum or plasma comprising both maternal and fetal DNA), and a peripherally-derived somatic sample (e.g., blood, serum or plasma comprising different cell types, e.g., hematopoietic cells, mesenchymal cells, and circulating cells from other organ systems). Mixed samples include samples with genomic material from two different sources, which may be sources from a single individual, e.g., normal and atypical somatic cells; cells that are from two different individuals, e.g., a sample with both maternal and fetal genomic material or a sample from a transplant patient that comprises cells from both the donor and recipient; or samples with nucleic acids from two or more sources from different organisms, e.g., the mammalian host and an infectious organism such as a virus, bacteria, fungus, parasite, etc.

As used herein "nucleotide" refers to a base-sugar-phosphate combination which is a monomeric unit of a nucleic acid sequence (DNA and RNA). A nucleotide sequence refers to identification of the particular base for the nucleotide.

The terms "sequencing", "sequence determination" and the like as used herein refers generally to any and all biochemical processes that may be used to determine the order of nucleotide bases in a nucleic acid.

The term "set of loci" when used to determine CNV for a genomic region refers to two or more loci that are located within or associated with a genomic region. The copy number variation within a particular genomic region can be determined by measuring the copy number of the loci within the set of loci, and their relationship allows identification of copy number variation for a genomic region.

The Invention in General

This invention relates to processes for calculating the CNV of one or more genomic regions by comparison of frequency of the genomic regions to the source contribution of nucleic acids from different sources within a mixed sample. The present invention uses systems that process empirical information provided for distinguishing regions of informative loci to determine contribution of cell free nucleic acids from different sources within a sample. The CNV can be determined for larger genomic regions using selected sets of loci which are located in or are associated with the genomic region of interest.

The CNV for a genomic region can be calculated by comparison of the copy number or frequency of the genomic region from a particular source to a calculated "baseline" level of the contribution of nucleic acids from that source in a mixed sample. Such baseline numbers are preferably empirically determined, as described in more detail herein, although a reference baseline level can be used in specific embodiments.

The processes of the invention in many embodiments utilize binomial probability distributions to determine the percentage of nucleic acids from the different sources in a mixed sample. Such binomial distributions can allow the calculation of source contribution of cell free nucleic acids from a first source and a second source in a mixed sample. This information can be used along with counts of genomic regions of interest to determine any change in copy number of the genomic regions that deviate from the relative source contribution of the nucleic acids from the minor and/or first source. For larger genomic regions, counts of two or more selected loci can be used to determine the copy number variation for the genomic region and, in certain aspects, to define the size of the region that displays CNV in the mixed sample.

The source contribution can be determined in the processes and systems of the invention through utilization of informative loci with distinguishing regions that allow differentiation of nucleic acids from the different sources. Detection of the frequency of these informative loci within a sample can be detected using multiple mechanisms, including hybridization. Preferably, source contribution of nucleic acids from different sources within a mixed sample is determined by sequence determination of the isolated copies of nucleic acids corresponding to informative loci from the sources in the mixed sample. The number of individual informative loci used to determine source contribution may be 2 or more, preferably 4 or more, preferably 8 or more, preferably 16 or more, preferably 32 or more, preferably 64 or more, and most preferably 96 or more.

Multiple mechanisms for identifying the distinguishing regions within an informative locus can be used in the processes of the invention. For example, source contribution of cell free DNA in a sample from a single individual can be determined by sequencing copies of two or more informative loci present in a mixed sample. For each informative locus, counts for both alleles (signified herein as A and B) present in the mixed sample are determined. With an observation of counts $A \leq B$, A is the count for the less abundant allele of the informative locus (corresponding to the second source DNA) and B is the count for the more abundant allele (corresponding to the first source DNA).

Statistically, this environment is modeled by a binomial distribution with some probability p of sequencing the A allele in a mixture of A and B alleles:

$$\text{Binomial}(A, B, p) = \frac{(A+B)!}{A!B!} p^A (1-p)^B.$$

Since A and B are known, the probability p is the informative value. The value p* of p that maximizes the value of Binomial(A, B, p) is considered the maximum likelihood estimate for the binomial distribution with counts A and B.

For example, since fetal DNA is expected to be less prevalent in maternal plasma, the probability p of sequencing the A allele corresponds to a measure of fetal enrichment f using the following formula:

$$f = 2*p.$$

The best (most likely) estimate of fetal enrichment given the A and B counts is when p=p*.

A more accurate calculation of the source contribution of cell free nucleic acids from a mixed sample can be calculated using sequence determination of several informative loci within the mixed sample. The use of multiple loci in determining second source percent DNA contribution increases the likelihood that the percentage is truly representative, as measurement of frequency of a single informative locus may not be truly indicative of the level of all second source DNA.

In order to determine the percentage of cell free nucleic acids from a first source and/or a second source within a mixed sample, the sequence of a statistically significant number of copies of several informative loci is determined. The counts of the different polymorphisms in the loci are used to calculate the source contribution of the cell free nucleic acids from the sources within the mixed sample, with $A_i$ and $B_i$ representative of the counts of the A and B alleles for the ith locus. For example, for 20 informative loci sequenced, each one individually is referred to as the 1st, 2nd, 3rd, . . . , 20th. Thus $A_5$ and $B_5$ are the counts for the A and B alleles of the 5th locus.

The probability p of sequencing A alleles from these multiple measurements corresponds to a measure of enrichment of the DNA from the second source. Each $A_i$, $B_i$ pair of counts for the ith locus, however, has a different best estimate $p_i*$ for the probability of sequencing an A allele. This is addressed by utilizing the product of many binomial distributions corresponding to informative loci that have been measured:

$$\prod_i \text{Binomial}(A_i, B_i, p).$$

The value of p that maximizes this product is denoted p*, and just as before gives the best estimate of enrichment of the second source DNA when p=p*. The p* can be identified using any number of standard optimization algorithms, as described in more detail below. Frequently a logarithmic transformation is applied to the product to make the computations easier, while still producing the same result.

In a more specific example, an accurate estimation of fetal DNA frequency can be determined using the processes of the invention with a relatively tight confidence interval, regardless of the gender of the fetus. This approach differs from processes which utilize Y chromosome sequences derived from male fetuses for fetal frequency estimation (Fan et al., Proc Natl Acad Sci USA. 2008 Oct. 21; 105 (42):16266-71. Epub 2008 Oct. 6; Lun F M et al., Proc Natl Acad Sci USA. 2008 Dec. 16; 105(50):19920-5. Epub 2008 Dec. 5). This approach also differs from other processes in that it employs a direct allelic identification approach rather than an indirect measure of either probe hybridization during real time PCR (Lun F M et al., Clin Chem. 2008 October; 54(10):1664-72. Epub 2008 Aug. 14) or band intensity following electrophoresis (Dhallan et al., Lancet. 2007 Feb. 10; 369(9560):474-81). Importantly, the invention utilizes multiple informative loci to determine fetal allele frequency, and the accuracy of the estimation can be improved by reducing the deviation of the different best estimate $p_i*$ for each individual locus. Accuracy can also be increased by using additional loci in determination of p.

Detection of informative loci for use in the processes of the invention can be carried out using various techniques known to those skilled in the art. These include, but are not limited to, those described in U.S. Pat. No. 6,258,540, issued to Lo and Wainscoat; U.S. Pat. Nos. 7,901,884, 7,754,428, 7,718,367, 7,709,194, and 7,645,576 issued to Lo et al; U.S. Pat. No. 7,888,017 issued to Quake et al.; Chiu R W, et al. 2008. U.S. Pat. Nos. 7,727,720 and 7,718,370, 7,442,506, 7,332,277, 7,208,274 and 6,977,162, issued to Dhallan; U.S. Pat. No. 7,799,531, issued to Mitchell and Mitchell; U.S. Pat. No. 7,582,420, issued to Oliphant et al. U.S. application Ser. No. 13/013,732 (Oliphant et al.), *Proc Natl Acad Sci USA* 105: 20458-20463; Dhallan et al. 2007 *Lancet* 369: 474-481; Fan H C et al., 2008 *Proc Natl Acad Sci* 105: 16266-16271; Fan H C et al., 2010 Clinical Chemistry 56:8; 1279-1286 Lo Y M et al., *Proc Natl Acad Sci USA* 104: 13116-13121; Lun F M, Chiu R W et al., 2008 *Clin Chem* 54: 1664-1672; Lun F M et al., *Proc Natl Acad Sci USA* 105: 19920-19925, each of which are incorporated by reference herein.

In a preferred aspect, the distinguishing regions of the informative loci in the mixed sample are detected in a manner to maximize the counts detected for A and B values of each informative locus. This can be done, for example, by performing multiple identification reactions for the distinguishing regions at each locus. This reduces the bias in allele count that may be introduced from the experimental activities used to obtain the counts. The estimation of second source DNA is thus more accurate with a tighter confidence interval.

Figure 1:
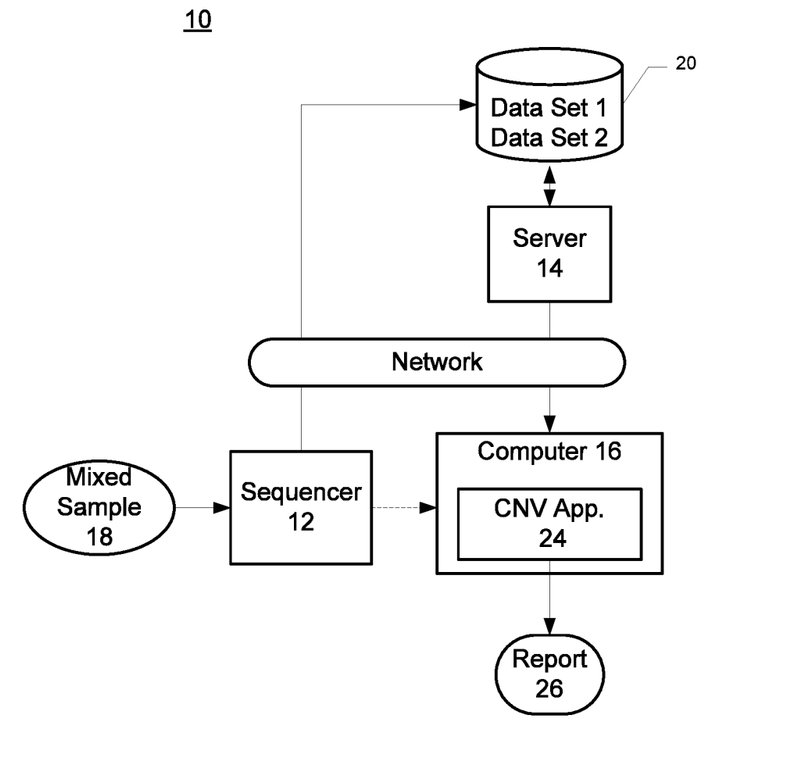
FIG. 1 is a block diagram illustrating an exemplary system environment.

FIG. 1 is a block diagram illustrating an exemplary system environment in which one embodiment of the present invention may be implemented for determining contribution of cell free nucleic acids from the first source and/or second source in a mixed sample. The system 10 includes a DNA sequencer 12, a server 14 and a computer 16. The DNA sequencer 12 may be coupled to the server 14 and/or the computer directly or through a network. The computer 16 may be in communication with the server 14 through the same or different network.

In one embodiment, a mixed sample 18 is input to the DNA sequencer 12. In one embodiment, the mixed sample 18 may comprise maternal and fetal cell free nucleic acids that contain cell free nucleic acids from normal cells and cancer cells. The DNA sequencer 12 may be any commercially available instrument that automates the DNA sequencing process for sequence analysis of oligonucleotides present in the mixed sample 18. The output of the DNA sequencer 12 may be in the form of first and second data sets 20 comprising frequency data for one or more informed and loci from first and second sources. In one embodiment, the first and second data sets 20 may be stored in a database that is accessible by the server 14.

According to the exemplary embodiment, the computer 16 executes a software component, referred to herein as the copy number variation (CNV) application 24, that calculates CNV for one or more genomic regions in the mixed sample 18 by comparison of frequency of the genomic regions to the source contribution of nucleic acids from different sources within the mixed sample 18. In one embodiment, the computer 16 may comprise a personal computer, but the computer 16 may comprise any type of machine that includes at least one processor and memory.

The output of the copy number variation application 24 is a report 26 listing the CNV. The report 26 may be paper that is printed out, or electronic, which may be displayed on a monitor and/or communicated electronically to users via e-mail, FTP, text messaging, posted on a server, and the like.

Although the application 24 is shown as being implemented as software, the application 24 may be implemented as a combination of hardware and software. In addition, the application 24 may be implemented as multiple components operating on the same or different computers.

Both the server 14 and the computer 16 may include hardware components of typical computing devices (not shown), including a processor, input devices (e.g., keyboard, pointing device, microphone for voice commands, buttons, touchscreen, etc.), and output devices (e.g., a display device, speakers, and the like). The server 14 and computer 16 may include computer-readable media, e.g., memory and storage devices (e.g., flash memory, hard drive, optical disk drive, magnetic disk drive, and the like) containing computer instructions that implement the functionality disclosed when executed by the processor. The server 14 and the computer 16 may further include wired or wireless network communication interfaces for communication.

Although the server 14 and computer 16 are shown as single computers, it should be understood that they could be multiple servers and computers, and the functionality of the copy number variation application 24 may be implemented using a different number of software components. For example, the copy number variation application 24 may be implemented as more than one component.

Optimization Algorithms for Use with the Invention

The probability p* that provides the best fit for p in the determination of the maximum likelihood estimate can be further refined using an optimization algorithm. Thus, in a preferred embodiment, the maximum likelihood estimate is calculated using an optimization algorithm to provide an iterative process for determining probability p that best fits the data of the two data sets. The optimization algorithm can be any algorithm that can determine the best fit for probability p based on the empirical informative loci data. Examples of such optimization algorithms include gradient descent, simulated annealing, or evolutionary algorithms. Simulated annealing (SA) is a generic probabilistic metaheuristic for the global optimization problem of locating a good approximation to the global optimum of a given function in a large search space. It is often used when the search space is discrete (e.g., all tours that visit a given set of cities). For certain problems, simulated annealing may be more effective than exhaustive enumeration—provided that the goal is merely to find an acceptably good solution in a fixed amount of time, rather than the best possible solution.

In other aspects, the algorithm is an evolutionary algorithm, which is a search heuristic that mimics the process of natural evolution. Evolutionary algorithms generate solutions to optimization problems using techniques inspired by natural evolution, such as inheritance, mutation, selection, and crossover.

In yet other aspects, the algorithm used in gradient descent, also known as steepest descent, or the process of steepest descent. Gradient descent is a first-order optimization algorithm. To find a local minimum of a function using gradient descent, one takes steps proportional to the negative of the gradient (or of the approximate gradient) of the function at the current point. If instead one takes steps proportional to the positive of the gradient, one approaches a local maximum of that function.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for.

Example 1

Calculation of Source Contribution Using a Single Locus

In order to determine the percentage of a cfDNA from a single source within a mixed sample, the sequence of a statistically significant number of copies of an informative locus is determined. The counts of the different polymorphisms in the loci are used to calculate the source contribution of the cfDNA from the first source and/or the second source within the mixed sample.

In an informative locus with a single polymorphism, following sequence determination of the first allele (A) and the second allele (B), the number of alleles present in the sample are found empirically to be A=10 and B=100. The source contribution (p) of the second source allele, A, is determined using the following equation:

$$\text{Binomial}(10, 100, p) = \frac{110!}{10!100!} p^{10}(1-p)^{100}.$$

For optimization, the m/e function of the R statistical software system, version release 2.12.2 was used to perform all binomial calculations. Using the m/e function in the R statistical software system, p* was estimated to be 0.09091285, which corresponds to a fetal enrichment of f=2*p*=0.1818257.

Example 2

Calculation of Second Source Contribution Using Multiple Loci

In order to determine the percentage of cfDNA from a single source within a mixed sample using multiple loci, the sequence of a statistically significant number of copies of two or more informative loci were determined. The counts of the different polymorphisms in the loci were used to calculate the source contribution of the cfDNA from the first source and/or the second source within the mixed sample.

In a first example using multiple loci from a maternal sample comprising both maternal and fetal cfDNA, five informative loci with the following counts for the A and B alleles were determined empirically:

| I | $A_i$ | $B_i$ |
|---|-------|-------|
| 1 | 10 | 100 |
| 2 | 8  | 90  |
| 3 | 11 | 99  |
| 4 | 13 | 124 |
| 5 | 9  | 113 |

As reported the maximum likelihood estimate is:

$p^* = 0.08839108$ and the fetal % is $f = 2 \cdot p^* = 0.1767822$

The process of the invention was then used to find the p* that maximizes the product:

Binomial(10,100,$p$)*Binomial(8,90,$p$)*Binomial(11,99,$p$)*Binomial(13,124,$p$)*Binomial(9,113,$p$).

Using the mle function in the R statistical software system, version release 2.12.2, the p* was estimated to be 0.08839108, corresponding to a fetal enrichment estimate of $f = 2 \cdot p^* = 0.1767822$

Example 3

Calculation of CNV of an Informative Locus

The approach described in Example 2 using binomials was used to determine source contribution of fetal nucleic acids in a maternal sample. In addition, a more standard ratio-based method described in Chu et al., *Prenat Diagn* 2010; 30: 1226-1229 was also used to derive an estimation of the percent fetal contribution in a maternal sample. These numbers generated empirically from which the percent fetal contribution was determined were in turn used to identify loci in which the CNV varied by at least 50% from the estimated source contribution of the fetal DNA in the maternal sample. Table 1 summarizes the data and the calculation of percent fetal in the sample:

TABLE 1

Determination of Percent Fetal cfDNA for a First Maternal Sample Using 49 Informative Loci

| Sample 1 Loci | $A_i$ Counts | $B_i$ Counts | Binomial Percent Fetal Calculation | Chu et al., Percent Fetal Calculation |
|---|---|---|---|---|
| Ch01_Lc1 | 42 | 793 | 0.078836119 | 0.078820769 |
| Ch01_Lc2 | 34 | 744 | | |
| Ch01_Lc3 | 22 | 927 | | |
| Ch01_Lc4 | 28 | 552 | | |
| Ch01_Lc5 | 13 | 826 | | |
| Ch01_Lc6 | 37 | 753 | | |
| Ch01_Lc7 | 44 | 784 | | |
| Ch01_Lc8 | 18 | 482 | | |
| Ch02_Lc1 | 36 | 998 | | |
| Ch02_Lc2 | 52 | 1206 | | |
| Ch02_Lc3 | 45 | 844 | | |
| Ch03_Lc1 | 40 | 869 | | |
| Ch03_Lc2 | 20 | 516 | | |
| Ch03_Lc3 | 35 | 851 | | |
| Ch03_Lc4 | 21 | 785 | | |
| Ch03_Lc5 | 64 | 1020 | | |
| Ch03_Lc6 | 33 | 979 | | |
| Ch03_Lc7 | 30 | 1159 | | |
| Ch04_Lc1 | 28 | 499 | | |
| Ch04_Lc2 | 47 | 810 | | |
| Ch04_Lc3 | 18 | 587 | | |
| Ch05_Lc1 | 61 | 1191 | | |
| Ch05_Lc2 | 15 | 899 | | |
| Ch05_Lc3 | 21 | 566 | | |
| Ch05_Lc4 | 40 | 772 | | |
| Ch05_Lc5 | 36 | 1031 | | |
| Ch06_Lc1 | 41 | 822 | | |
| Ch06_Lc2 | 65 | 1078 | | |
| Ch07_Lc1 | 31 | 831 | | |
| Ch07_Lc2 | 39 | 857 | | |
| Ch07_Lc3 | 48 | 1148 | | |
| Ch07_Lc4 | 25 | 876 | | |
| Ch08_Lc1 | 39 | 869 | | |
| Ch08_Lc2 | 17 | 491 | | |
| Ch08_Lc3 | 31 | 585 | | |
| Ch08_Lc4 | 42 | 840 | | |
| Ch08_Lc5 | 47 | 963 | | |
| Ch09_Lc1 | 20 | 571 | | |
| Ch09_Lc2 | 25 | 692 | | |
| Ch09_Lc3 | 23 | 543 | | |
| Ch09_Lc4 | 32 | 742 | | |
| Ch09_Lc5 | 20 | 988 | | |
| Ch10_Lc1 | 28 | 555 | | |
| Ch10_Lc2 | 15 | 664 | | |
| Ch10_Lc3 | 11 | 814 | | |
| Ch11_Lc1 | 39 | 1036 | | |
| Ch11_Lc2 | 38 | 661 | | |
| Ch11_Lc3 | 34 | 779 | | |
| Ch12_Lc1 | 38 | 713 | | |
| Ch12_Lc2 | 35 | 973 | | |

To identify loci exhibiting a statistically significant decrease in copy numbers of loci detected, the ratio of the individual loci was determined and compared to the calculated percent fetal cfDNA for the maternal sample. The numbers shown bolded above each displayed significantly lowered copy number of fetal DNA compared to the frequency of the maternal allele. The overall percent calculation of fetal cfDNA in the maternal sample was 7.8%. The following loci exhibited a fetal contribution 5-fold or less than the average, and thus a statistically decreased CNV:

| Locus | Fetal Cts | Maternal Cts | Ave % fetal | Locus % fetal | % Decrease |
|---|---|---|---|---|---|
| Ch01_Lc5 | 13 | 826 | 7.88% | 1.57% | 5.02-fold |
| Ch10_Lc3 | 11 | 814 | 7.88% | 1.35% | 5.84-fold |

The algorithm used for optimization of the maximum likelihood estimate was the "Broyden, Fletcher, Goldfarb, and Shanno" ("BFGS") method. The BFGS method is a gradient descent algorithm that approximates Newton's method. For optimization, the m/e function of the R statistical software system, version release 2.12.2 was used to perform all binomial calculations.

When compared to a weighted average approach introduced by Chu et al., the maximum likelihood estimate results from the binomial distribution approach presented above correlated with an R2>0.99 and a slope near 1.

Example 3

Calculation of CNV of a Genomic Region

As described above, the approach described in Example 2 using binomials was used to determine source contribution of fetal nucleic acids in a maternal sample.

In a separate assay, the mixed sample was analyzed for loci found within the DiGeorge Syndrome Critical Region (DGCR) at chromosome 22q11. These loci include two loci on either end of the velo-cardio facial syndrome region at 22q11.2, and the loci known to be involved in conotruncal cardiac disease. A total of 32 loci in all spanning the DGCR are used to determine the presence of a possible deletion and the boundaries of any deletion that may be present in a mixed sample.

In a first sample, the percent fetal DNA in the maternal sample is determined to be approximately 9.2% using the methods of Example 2. The loci in the DGCR are differentiated in the maternal and fetal sources in a separate assay through the identification of polymorphisms in the selected loci of the set used to determine the presence or absence of a deletion at 22q11. All fetal 22q11 loci of the set of selected loci spanning the DGCR are found to be present in the maternal sample at a variance of from approximately 8.9-9.3% of the total amount of selected loci in the maternal sample, and so no deletion is detected in this sample.

In a second sample, the percent fetal DNA in the maternal sample is determined to be approximately 10.4% using the methods of Example 2. All fetal 22q11 loci of the set of selected loci are found to be present in the maternal sample at a variance of from approximately 4.8-5.4% of the total amount of selected loci in the maternal sample. This is consistent with a deletion of one DGCR at chromosome 22 from paternal origin.

A process and system for estimating copy number variation of selected loci from a first source and a second source in a mixed sample has been disclosed. The present invention has been described in accordance with the implementations shown, and there could be variations to the implementations, and any variations would be within the spirit and scope of the present invention. For example, the exemplary embodiment can be implemented using hardware, software, a computer readable medium containing program instructions, or a combination thereof. Software written according to the present invention is to be either stored in some form of computer-readable medium such as a memory, a hard disk, or a CD/DVD-ROM and is to be executed by a processor. Accordingly, many modifications may be made by one of ordinary skill in the art without departing from the spirit and scope of the appended claims. In the claims that follow, unless the term "means" is used, none of the features or elements recited therein should be construed as means-plus-function limitations pursuant to 35 U.S.C. § 112, ¶6.

What is claimed is:

1. A computer-implemented process for calculating copy number variation (CNV) of one or more genomic regions in a single source in a mixed sample of DNA from blood, serum or plasma of a patient, the mixed sample including a minor source and a major source, the process comprising the steps of:
   a) measuring a frequency of thirty-two or more informative loci from a first source comprising the minor source and a frequency of thirty-two or more informative loci from a second source comprising the major source;
   b) accessing, by a computer processor, a first data set comprising frequency data based on identification of distinguishing regions of the thirty-two or more informative loci from the first source as the single source in the mixed sample;
   c) accessing, by the computer processor, a second data set comprising frequency data based on identification of distinguishing regions of the thirty-two or more informative loci from the second source as the single source in the mixed sample;
   d) calculating, by the computer processor, an estimated source contribution of cell free nucleic acids based on a binomial distribution of counts of the distinguishing regions from the first and second data sets;
   e) accessing, by the computer processor, a third data set comprising frequency data for two or more genomic regions from the combined first and second sources in the mixed sample; and
   f) calculating, by the computer processor, a presence or absence of a CNV for one or more genomic regions by comparison of the frequency data from the two or more genomic regions from the combined first and second sources and the estimated contribution of cell free nucleic acids in the mixed sample.

2. The computer-implemented process of claim 1, wherein the CNV is determined for one or more genomic regions in the second source of the mixed sample, and wherein the CNV for the one or more genomic regions is calculated based on the contribution of the second source to the mixed sample.

3. The computer-implemented process of claim 1, wherein the frequency data comprises counts for a set of loci located in or associated with a genomic region.

4. The computer-implemented process of claim 1, wherein the mixed sample comprises cell free nucleic acids from both normal and putative genetically atypical cells.

5. The computer-implemented process of claim 1, wherein the contribution is quantified by calculating a maximum likelihood estimate based on the quantity of the thirty-two or more informative loci from the first source and the second source.

6. The computer-implemented process of claim 5, wherein the maximum likelihood estimate is modeled by the equation:

$$Binomial(A, B, p) = \frac{(A+B)!}{A!B!}p^A(1-p)^B$$

wherein A is the quantity of the thirty-two or more informative loci from the second source, B is the quantity of the thirty-two or more informative loci from the first source, and p is the maximum likelihood estimate for the binomial distribution with quantities A and B.

7. The computer-implemented process of claim 6, wherein the p corresponding to the maximum likelihood estimate is calculated using an optimization algorithm.

8. The computer-implemented process of claim 1, wherein the frequency data for thirty-two or more informative loci from the first source and the second source does not include the data from the two or more genomic regions.

9. The computer-implemented process of claim 1, wherein the first data set comprising frequency data is based on the identification of distinguishing regions of at least 96 informative loci.

10. The computer-implemented process of claim 1, wherein the first data set comprising frequency data is based on the identification of distinguishing regions of at least 64 informative loci.

11. The computer-implemented process of claim 1, wherein the patient includes a diagnosed or undiagnosed condition.

12. The computer-implemented process of claim 11, further comprising:
   assisting in a communication of the presence or absence of the CNV to the patient, the presence or absence of the CNV being related to the diagnosed or undiagnosed condition of the patient.

13. The computer-implemented process of claim 1, wherein the patient is a pregnant mammal.

14. The computer-implemented process of claim 1, wherein the major source comprises maternal cell free nucleic acids and the minor source comprises fetal cell free nucleic acids.

* * * * *